United States Patent
Kim (10) Patent No.: US 9,844,584 B2
(45) Date of Patent: Dec. 19, 2017

(54) COMPOSITION FOR PREVENTING OR TREATING SEPSIS

(71) Applicants: GemVax & KAEL Co., Ltd., Daejeon (KR); Sang Jae Kim, Seoul (KR)

(72) Inventor: Sang Jae Kim, Seoul (KR)

(73) Assignee: GEMVAX & KAEL CO., LTD. (KR)

( * ) Notice: Subject to any disclaimer, the term of this patent is extended or adjusted under 35 U.S.C. 154(b) by 0 days.

(21) Appl. No.: 14/400,293

(22) PCT Filed: May 10, 2013

(86) PCT No.: PCT/KR2013/004145
§ 371 (c)(1),
(2) Date: Sep. 9, 2015

(87) PCT Pub. No.: WO2013/169060
PCT Pub. Date: Nov. 14, 2013

(65) Prior Publication Data
US 2016/0008438 A1 Jan. 14, 2016

(30) Foreign Application Priority Data

| May 11, 2012 | (KR) | 10-2012-0050529 |
| May 11, 2012 | (KR) | 10-2012-0050533 |
| Jul. 2, 2012 | (KR) | 10-2012-0071989 |
| Sep. 19, 2012 | (KR) | 10-2012-0104207 |

(51) Int. Cl.
| *A61K 38/45* | (2006.01) |
| *A61K 38/10* | (2006.01) |
| *A61K 9/00* | (2006.01) |
| *C12N 9/12* | (2006.01) |
| *A23L 33/18* | (2016.01) |
| *A61K 38/00* | (2006.01) |

(52) U.S. Cl.
CPC ............. *A61K 38/45* (2013.01); *A23L 33/18* (2016.08); *A61K 9/0019* (2013.01); *A61K 38/10* (2013.01); *C12N 9/1276* (2013.01); *A23V 2002/00* (2013.01); *A61K 38/00* (2013.01); *C12Y 207/07049* (2013.01)

(58) Field of Classification Search
None
See application file for complete search history.

(56) References Cited

U.S. PATENT DOCUMENTS

| 6,967,211 B2 | 11/2005 | Inoue |
| 7,030,211 B1 | 4/2006 | Gaudernack et al. |
| 7,794,723 B2 | 9/2010 | Gaudernack et al. |
| 8,828,403 B2 | 9/2014 | Filaci et al. |
| 8,933,197 B2 | 1/2015 | Stemmer et al. |
| 9,023,987 B2 | 5/2015 | Chung et al. |
| 9,540,419 B2 | 1/2017 | Kim et al. |
| 9,572,858 B2 | 2/2017 | Kim |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1* | 4/2015 | Kim .................. C07K 14/4703 514/1.5 |
| 2015/0099693 A1* | 4/2015 | Kim .................. C07K 14/4703 514/1.9 |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |

(Continued)

FOREIGN PATENT DOCUMENTS

| EP | 1020190 A3 | 10/2000 |
| EP | 1093381 B2 | 7/2009 |

(Continued)

OTHER PUBLICATIONS

Beer, T.M., et al., "Phase II Study of Weekly Docetaxel in Symptomatic Androgen-independent Prostate Cancer," Annals of Oncology 12(9):1273-1279, Oxford University Press, England (2001).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Calderwood, S.K., et al., "Heat Shock Proteins in Cancer: Chaperones of Tumorigenesis," Trends in Biochemical Sciences 31(3):164-172, Elsevier Trends Journals, England (2006).
Dempsey, N.C., et al., "Differential Heat Shock Protein Localization in Chronic Lymphocytic Leukemia," Journal of Leukocyte Biology 87(3):467-476, Society for Leukocyte Biology, United States (2010).

(Continued)

*Primary Examiner* — Christina Bradley
(74) *Attorney, Agent, or Firm* — Sterne, Kessler, Goldstein and Fox P.L.L.C.

(57) ABSTRACT

Provided in the present invention is a peptide for preventing or treating sepsis. The peptide can improve symptoms of sepsis by inhibiting production of TNF, IL-1, and IL-6, which are cytokines that are related to sepsis, or can prevent or treat sepsis. Also disclosed are a pharmaceutical composition or a food composition containing the peptide as an active ingredient, a usage of the peptide for preventing or treating sepsis, and a kit comprising the peptide and instructions.

12 Claims, 2 Drawing Sheets

(56) References Cited

U.S. PATENT DOCUMENTS

| | | |
|---|---|---|
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |

FOREIGN PATENT DOCUMENTS

| | | |
|---|---|---|
| EP | 1817337 B1 | 1/2011 |
| JP | 2010252810 A | 11/2010 |
| JP | 5577472 B2 | 8/2014 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 2010005841 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120087885 A | 8/2012 |
| KR | 20120121196 A | 11/2012 |
| KR | 20120130996 A | 12/2012 |
| KR | 20120133661 A | 12/2012 |
| WO | WO-0002581 A1 | 1/2000 |
| WO | WO-2010003520 A2 | 1/2010 |
| WO | WO-2010012850 A1 | 2/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |

OTHER PUBLICATIONS

Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).

Eustace, B.K. and Jay, D.G., "Extracellular Roles for the Molecular Chaperone, Hsp90," Cell Cycle 3(9):1098-1100, Taylor & Francis, United States (2004).

Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).

Evans, C.G., et al., "Heat Shock Protein 70 (Hsp70) as an Emerging Drug Target," Journal of Medicinal Chemistry 53(12):4585-4602, American Chemical Society, United States (2010).

Ferrarini, M., et al., "Unusual Expression and Localization of Heat-shock Proteins in Human Tumor Cells," International Journal of Cancer51(4):613-619, Wiley-Liss, United States (1992).

Garcia-Carbonero, R., et al., "Inhibition of HSP90 Molecular Chaperones: Moving Into the Clinic," The Lancet Oncology 14(9):e358-e369, Lancet Publishing Group, England (2013).

Henry, J.Y., et al., "Lenalidomide Enhances the Anti-prostate Cancer Activity of Docetaxel in vitro and in vivo," The Prostate 72(8):856-867, Wiley-Liss, United States (2012).

International Preliminary Report on Patentability for International Application No. PCT/KR2014/011280, The International Bureau of WIPO, Geneva, Switzerland, dated May 24, 2016, 15 pages.

International Search Report for International Application No. PCT/KR2014/011280, Korean Intellectual Property Office, Republic of Korea, dated Feb. 11, 2015, 12 pages.

International Search Report for International Application No. PCT/KR2014/012502, Korean Intellectual Property Office, Republic of Korea, dated Mar. 11, 2015, 10 pages.

International Preliminary Report on Patentability for International Application No. PCT/KR2014/012502, The International Bureau of WIPO, Geneva, Switzerland, dated Jun. 21, 2016, 22 pages.

Jaattela, M., "Over-expression of Hsp70 Confers Tumorigenicity to Mouse Fibrosarcoma Cells," International Journal of Cancer 60(5):689-693, Wiley-Liss, United States (1995).

Jemal, A., et al., "Cancer Statistics, 2008," CA: A Cancer Journal for Clinicians 58(2):71-96, Wiley, United States (2008).

Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).

Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).

Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).

Morano, K.A., "New Tricks for an Old Dog: the Evolving World of Hsp70," Annals of the New York Academy of Sciences 1113:1-14, Blackwell, United States (2007).

Murphy, M.E., "The Hsp70 Family and Cancer," Carcinogenesis 34(6):1181-1188, Irl Press, England (2013).

Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).

Pfosser, A., et al., "Liposomal HSP90 Cdna Induces Neovascularization via Nitric Oxide in Chronic Ischemia," Cardiovascular Research 65(3):728-736, Oxford Journals, England (2005).

Powers, M.V., et al., "Targeting HSP70: the Second Potentially Druggable Heat Shock Protein and Molecular Chaperone?," Cell Cycle 9(8):1542-1550, Taylor & Francis, United States (2010).

Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).

Seo, J.S., et al., "T Cell Lymphoma in Transgenic Mice Expressing the Human Hsp70 Gene," Biochemical and Biophysical Research Communications 218(2):582-587, Elsevier, United States (1996).

Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).

Uehara, Y., "Natural Product Origins of Hsp90 Inhibitors," Current Cancer Drug Targets 3(5):325-330, Bentham Science Publishers, Netherlands (2003).

(56) References Cited

OTHER PUBLICATIONS

Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Volloch, V.Z. and Sherman, M.Y., "Oncogenic Potential of Hsp72," Oncogene 18(24):3648-3651, Nature Publishing Group, England (1999).
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "Pl3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Altschul, S.F., et al., "Basic Local Alignment Search Tool," Journal of Molecular Biology 215(3):403-410, Elsevier, England (1990).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Cho, Y.J., "GemVax & Kael (082270)," Hana Daetoo Securities, Company Report, Sep. 10, 2012, 8 pages.
Choi, S.G., "Recent Advances in Cancer Cachexia," Journal of Korean Oncology Nursing 11(1):20-25 (2011).
Co-pending U.S. Appl. No. 14/413,732, inventor Sang Jae Kim, filed Jul. 11, 2013 (Not Published).
Co-pending U.S. Appl. No. 14/896,358, inventor Sang Jae Kim, filed Dec. 4, 2015 (Not Published).
Co-pending U.S. Appl. No. 14/899,746, inventor Sang Jae Kim, filed Apr. 12, 2015 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dinarello, C.A., "Interleukin-1 in the Pathogenesis and Treatment of Inflammatory Diseases," Blood 117(14):3720-3732, American Society of Hematology, United States (2011).
Engineer, D.R. and Garcia, J.M., "Leptin in Anorexia and Cachexia Syndrome," International Journal of Peptides 2012:Article ID 287457, Hindawi Publishing Corporation, United States (2012).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
GemVax Receives Report on Anti-Inflammatory Mechanism, The Asia Economy Daily, Article written on May 7, 2013.

Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014,14 pages.
International Preliminary Report on Patentability for International Application No. PCT/KR2013/004176, The International Bureau of WIPO, Switzerland, dated Nov. 11, 2014,14pages.
International Preliminary Report on Patentability for International Application No. PCT/KR2013/006218, The International Bureau of WIPO, Switzerland, dated Jan. 13, 2015,27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/EP2013/059460, European Patent Office, Netherlands, dated Jul. 3, 2013, 5 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.

(56) References Cited

OTHER PUBLICATIONS

International Search Report for International Patent Application No. PCT/KR2013/004156, Korean Intellectual Property Office, Republic of Korea, dated Aug. 14, 2013, 10 pages.

International Search Report for International Application No. PCT/KR2013/008459, Korean Intellectual Property Office, Republic of Korea, dated Dec. 23, 2013, 8 pages.

Kern, K.A. and Norton, J.A., "Cancer Cachexia," Journal of Parenteral and Enteral Nutrition 12(3):286-298, Sage Publications, United States (1988).

Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).

Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).

Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).

Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).

Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).

Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).

Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).

Modica-Napolitano, J.S. and Singh, K.K., "Mitochondria as Targets for Detection and Treatment of Cancer," Expert Reviews in Molecular Medicine 4(9):1-19, Cambridge University Press, England (2002).

Myers, L.K., et al., "Collagen-Induced Arthritis, an Animal Model of Autoimmunity," Life Sciences 61(19):1861-1878, Elsevier, Netherlands (1997).

National Horizon Scanning Centre News on Emerging Technologies in Healthcare, GV1001 for Advanced and/or Metastatic Pancreatic Cancer, Published Apr. 2008.

NCBI, Reference Sequence: XP_003776612.1 (Jul. 17, 2012).

Novina, C.D. and Sharp, P.A., "The RNAi Revolution," Nature 430(6996):161-164, Nature Publishing Group, England (2004).

Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).

Pearson, W.R. and Lipman, D.J., "Improved Tools for Biological Sequence Comparison," Proceedings of the National Academy of Sciences USA 85(8):2444-2448, National Academy of Sciences, United States (1988).

Rana, T.M., "Illuminating the Silence: Understanding the Structure and Function of Small RNAs," Nature Reviews. Molecular Cell Biology 8(1):23-36, Nature Publishing Group, England (2007).

Roubenoff, R., et al., "Adjuvant Arthritis as a Model of Inflammatory Cachexia," Arthritis and Rheumatism 40(3):534-539, Wiley-Blackwell, United States (1997).

Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).

Smith, T.F. and Waterman, M.S., "Comparison of Biosequences," Advances in Applied Mathematics 2(4):482-489, Academic Press, Inc., United States (1981).

Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.

Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).

Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).

Tisdale, M.J., "Mechanisms of Cancer Cachexia," Physiological Reviews 89(2):381-410, American Physiological Society, United States (2009).

Tomari Y. and Zamore, P.D., "Perspective: Machines for RNAi," Genes and Development 19(5):517-529, Cold Spring Harbor Laboratory Press, United States (2005).

Vennela, B., et al., "Current and Future Strategies for Therapy of Pancreatic Cancer," International Journal of Research in Pharmacy and Medicine 2(3):728-740 (2012).

Walsmith, J. and Roubenoff, R., "Cachexia in Rheumatoid Arthritis," International Journal of Cardiology 85(1):89-99, Elsevier, Netherlands (2002).

Written Opinion for International Application No. PCT/EP2013/059460, European Patent Office, Germany, dated Jul. 3, 2013, 4 pages.

Written Opinion for International Application No. PCT/KR2013/004176, Korean Intellectual Property Office, Republic of Korea, dated Aug. 6, 2013, 13 pages.

Written Opinion for International Application No. PCT/KR2013/006218, Korean Intellectual Property Office, Republic of Korea, dated Sep. 26, 2013, 26 pages.

Written Opinion for International Application No. PCT/KR2013/008438, Korean Intellectual Property Office, Republic of Korea, dated Dec. 23, 2013, 9 pages.

Written Opinion for International Application No. PCT/KR2013/008445, Korean Intellectual Property Office, Republic of Korea, dated Dec. 23, 2013, 12 pages.

Written Opinion for International Application No. PCT/KR2014/005031, Korean Intellectual Property Office, Republic of Korea, dated Sep. 22, 2014, 7 pages.

Written Opinion for International Application No. PCT/KR2014/005508, Korean Intellectual Property Office, Republic of Korea, dated Oct. 14, 2014, 13 pages.

Written Opinion for International Application No. PCT/KR2013/008459, Korean Intellectual Property Office, Republic of Korea, dated Dec. 23, 2013, 9 pages.

Written Opinion for International Patent Application No. PCT/KR2013/004156, Korean Intellectual Property Office, Republic of Korea, dated Aug. 14, 2013, 13 pages.

Written Opinion for International Application No. PCT/KR2014/003425, Korean Intellectual Property Office, Republic of Korea, dated Jul. 21, 2014, 13 pages.

Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).

International Search Report for International Application No. PCT/KR2014/010035, Korean Intellectual Property Office, Republic of Korea, dated Feb. 2, 2015, 8 pages.

Shay, J.W., et al., "Telomerase therapeutics for cancer: challenges and new directions," Nature Reviews Drug Discovery 5(7): 577-584, Nature Publishing Group, England (2006).

(56) References Cited

OTHER PUBLICATIONS

Brandenburg, K., et al., "Peptide-based Treatment of Sepsis," Applied Microbiology and Biotechnology 90(3):799-808, Springer International, Germany (2011).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, the Association, United States (2011).
International Searching Authority, International Search Report for International Application No. PCT/KR2013/004145, Korean Intellectual Property Office, Republic of Korea, dated Aug. 14, 2013, 10 pages.
Kyte, J.A., "Cancer Vaccination with Telomerase Peptide GV1001," Expert Opinion on Investigational Drugs 18(5):687-694, Taylor & Francis, England (2009).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).
Stevenson, C.L., "Advances in Peptide Pharmaceuticals," Current Pharmaceutical Biotechnology 10(1):122-137, Bentham Science Publishers, Netherlands (2009).
International Searching Authority, Written Opinion for International Application No. PCT/KR2013/004145, Korean Intellectual Property Office, Republic of Korea, dated Aug. 14, 2013, 13 pages.
Co-pending U.S. Appl. No. 14/400,299; inventor Sang Jae Kim; filed May 10, 2013 (Not Published).
Dementia from Merck Manual, accessed on Jul. 29, 2009, pp. 1-17.
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Rheumatoid Arthritis from Merck Manual, accessed on Apr. 21, 2016, pp. 1-18.
Schenk, D., et al., "Immunization with Amyloid-beta Attenuates Alzheimer-disease-like Pathology in the PDAPP Mouse," Nature 400(6740):173-177, Nature Publishing Group, England (1999).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Co-pending U.S. Appl. No. 15/346,870, inventors Kim, Sang Jae, filed Nov. 9, 2016 (Not Yet Published).
Eisenegger, C., et al., "The Role of Testosterone in Social Interaction," Trends in Cognitive Sciences 15(6):263-271, Elsevier Science, England (2011).
"Seoul National University Bundang Hospital excited because of '000'," Clinical trials of Dream Anticancer Drug without side effects with Kael & GemVax, 4 pages, Apr. 22, 2013.
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Guo, R.F., et al., "Regulatory Effects of Eotaxin on Acute Lung Inflammatory Injury," Journal of Immunology 166(8):5208-5218, American Association of Immunologists, United States (2001).

Heldin, C.H., et al., "TGF-Beta Signalling from Cell Membrane to Nucleus through SMAD Proteins," Nature 390(6659):465-471, Nature Publishing Group, England (1997).
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/010035, Korean Intellectual Property Office, Republic of Korea, dated Apr. 26, 2016, 13 pages.
International Search Report for International Application No. PCT/KR2014/004752, Korean Intellectual Property Office, Republic of Korea, dated Jan. 16, 2015, 10 pages.
International Search Report for International Application No. PCT/KR2015/003642, Korean Intellectual Property Office, Republic of Korea, dated Jul. 3, 2015, 8 pages.
Kawasaki, H., et al., "Detection and Evaluation of Activation of Various Cancer Antigenic Peptide-specific CTLs in Mature Dendritic Cells Used for Dendritic Cell Therapy," The21st International Congress of Personalized Medicine, Conference Program and Abstracts, Personalized Medicine Universe (Japanese edition) 4(Supplement 2): 2 pages, Oct. 17, 2015.
Massague, J., "Tgf-Beta Signal Transduction," Annual Review of Biochemistry 67:753-791, Annual Reviews, United States (1998).
Morishita, M., and Peppas, N.A., "Is the Oral Route Possible for Peptide and Protein Drug Delivery?," Drug Discovery Today 11(19-20):905-910, Elsevier Science Ltd., England (2006).
National Institute of Diabetes and Digestive and Kidney Diseases, "Prostate Enlargement: Benign Prostatic Hyperplasia;" Updated Sep. 2014, 14 pages.
Sasada, A., et al., "A Case of Elderly Patient With Lung Cancer Efficiently Treated With Dendritic Cell Immunotherapy," The 20th International Congress of Personalized Medicine, Conference Program and Abstracts, Personalized Medicine Universe (Japanese edition) 4(Supplement 1): 2 pages, May 24, 2015.
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Song, J., et al., "Characterization and Fate of Telomerase-Expressing Epithelia during Kidney Repair," Journal of the American Society of Nephrology 22(12):2256-2265, American Society of Nephrology, United States (2011).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/004752, Korean Intellectual Property Office, Republic of Korea, dated Jan. 16, 2015, 21 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).

* cited by examiner

SEQUENCE LISTING

<160> NUMBER OF SEQ ID NOS: 3

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

```
Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
    275                 280                 285

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670
```

-continued

Pro Gly Leu Leu Gly Ala Ser Val Leu Gly Leu Asp Asp Ile His Arg
675 680 685

Ala Trp Arg Thr Phe Val Leu Arg Val Arg Ala Gln Asp Pro Pro Pro
690 695 700

Glu Leu Tyr Phe Val Lys Val Asp Val Thr Gly Ala Tyr Asp Thr Ile
705 710 715 720

Pro Gln Asp Arg Leu Thr Glu Val Ile Ala Ser Ile Ile Lys Pro Gln
725 730 735

Asn Thr Tyr Cys Val Arg Arg Tyr Ala Val Val Gln Lys Ala Ala His
740 745 750

Gly His Val Arg Lys Ala Phe Lys Ser His Val Ser Thr Leu Thr Asp
755 760 765

Leu Gln Pro Tyr Met Arg Gln Phe Val Ala His Leu Gln Glu Thr Ser
770 775 780

Pro Leu Arg Asp Ala Val Val Ile Glu Gln Ser Ser Ser Leu Asn Glu
785 790 795 800

Ala Ser Ser Gly Leu Phe Asp Val Phe Leu Arg Phe Met Cys His His
805 810 815

Ala Val Arg Ile Arg Gly Lys Ser Tyr Val Gln Cys Gln Gly Ile Pro
820 825 830

Gln Gly Ser Ile Leu Ser Thr Leu Leu Cys Ser Leu Cys Tyr Gly Asp
835 840 845

Met Glu Asn Lys Leu Phe Ala Gly Ile Arg Arg Asp Gly Leu Leu Leu
850 855 860

Arg Leu Val Asp Asp Phe Leu Leu Val Thr Pro His Leu Thr His Ala
865 870 875 880

Lys Thr Phe Leu Arg Thr Leu Val Arg Gly Val Pro Glu Tyr Gly Cys
885 890 895

Val Val Asn Leu Arg Lys Thr Val Val Asn Phe Pro Val Glu Asp Glu
900 905 910

Ala Leu Gly Gly Thr Ala Phe Val Gln Met Pro Ala His Gly Leu Phe
915 920 925

Pro Trp Cys Gly Leu Leu Leu Asp Thr Arg Thr Leu Glu Val Gln Ser
930 935 940

Asp Tyr Ser Ser Tyr Ala Arg Thr Ser Ile Arg Ala Ser Leu Thr Phe
945 950 955 960

Asn Arg Gly Phe Lys Ala Gly Arg Asn Met Arg Arg Lys Leu Phe Gly
965 970 975

Val Leu Arg Leu Lys Cys His Ser Leu Phe Leu Asp Leu Gln Val Asn
980 985 990

Ser Leu Gln Thr Val Cys Thr Asn Ile Tyr Lys Ile Leu Leu Leu Gln
995 1000 1005

Ala Tyr Arg Phe His Ala Cys Val Leu Gln Leu Pro Phe His Gln
1010 1015 1020

Gln Val Trp Lys Asn Pro Thr Phe Phe Leu Arg Val Ile Ser Asp
1025 1030 1035

Thr Ala Ser Leu Cys Tyr Ser Ile Leu Lys Ala Lys Asn Ala Gly
1040 1045 1050

Met Ser Leu Gly Ala Lys Gly Ala Ala Gly Pro Leu Pro Ser Glu
1055 1060 1065

Ala Val Gln Trp Leu Cys His Gln Ala Phe Leu Leu Lys Leu Thr
1070 1075 1080

Arg His Arg Val Thr Tyr Val Pro Leu Leu Gly Ser Leu Arg Thr

-continued

```
                  1085                1090                1095
Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 3
<211> LENGTH: 48
<212> TYPE: DNA
<213> ORGANISM: Homo sapiens

<400> SEQUENCE: 3
gaagcgcgcc cggcgctgct gaccagccgc ctgcgcttta ttccgaaa        48
```

COMPOSITION FOR PREVENTING OR TREATING SEPSIS

BACKGROUND OF THE INVENTION

Technical Field

The techniques disclosed herein are compositions for preventing or treating sepsis, prevention of sepsis or treatment method, peptides for preventing or treating sepsis, and use of peptide for prevention or treatment of sepsis.

Background Art

Sepsis is a bacterial disease of addiction represented by its production and reproductive toxins into the blood or a potentially fetal whole-body inflammation. Cause of lesions in sepsis includes otitis media, skin maturation increases, pressure sores, pulmonary disease, tooth decay, cholecystitis, pyelitis, osteomyelitis, infected uterus, etc. However, there is also a place of pyogenic *bacillus* invasion are not sure. Pathogens are *Streptococcus, Staphylococcus aureus, Escherichia coli, Diplococcus pneumoniae, Pseudomonas aeruginosa*, fungi, and the like. Symptoms include sudden onset of high fever, chills and shaking, Arthralgia, headache, and malaise.

The number of pulse decreases, breathe faster, if severe, consciousness vanishes. Severe sepsis occurs, when sepsis imports pulmonary dysfunction, blood clots or other blood disorders, decreased urine production, or organ dysfunction such as mental status changes.

Organ dysfunction of severe sepsis causes blood pressure (hypotension) or diseases such as lactic acidosis, but it is related to the one or more organs of the insufficient blood flow, which is septic shock.

Korea patent publication No. 1020040045400 discloses a composition for the treatment of sepsis.

BRIEF SUMMARY OF THE INVENTION

Disclosure

Technical Problem

In an aspect, the purpose of the present invention is to prevention or to treatment of sepsis.

In an aspect, the purpose of the present invention is to improvement in symptoms of sepsis.

In an aspect, the purpose of the present invention is to prevention or treatment of septic shock.

In an aspect, the purpose of the present invention is to reduce the concentration of cytokine which related with sepsis.

In an aspect, the purpose of the present invention is to prevention or treatment of inflammation which induced sepsis or inflammation resulting from sepsis.

Technical Solution

In an aspect, the present invention relates to a composition, the composition, as an active ingredient, may include a peptide comprising the amino acid sequence of SEQ ID NO: 1, the peptide sequence having at least 80% sequence homology to the peptide or peptide fragment thereof.

In an aspect, the present invention relates to a method, the method comprising the peptide or fragment thereof in the prevention of sepsis peptide comprising a peptide having the amino acid sequence of SEQ ID NO: 1 in the amount effective, at least 80% sequence homology with the peptide sequence or a method of treatment or prevention of sepsis comprising administering to a subject in need of treatment.

In an aspect, the present invention relates to the use, the peptide comprising the amino acid sequence of SEQ ID NO: 1, the use of a peptide or fragment thereof in the prevention or treatment of sepsis peptide having a sequence homology of 80% or more and the peptide sequence.

In an aspect, the present invention relates to a peptide, wherein the peptide is for the prevention or treatment of sepsis comprising the amino acid sequence of SEQ ID NO: 1 peptide, wherein the peptide sequence having at least 80% sequence homology to the peptide or peptide fragment thereof.

In an aspect, the present invention relates to a kit, the kit may include the amino acid sequence of SEQ ID NO: 1 peptide, wherein the peptide sequence having at least 80% sequence homology to the peptide or peptide fragment thereof; dose of the peptide, the route of administration, dosage and the number of instructions which indicates one or more indications.

In an aspect, the fragment may be a fragment composed of three or more amino acids.

In an aspect, the peptides may be derived from the human telomerase.

In an aspect, the prevention or treatment of sepsis may be to prevent or to treat septic shock.

In an aspect, the peptide may be administered in the form of injection formulation.

In an aspect, the injection formulation may be formulated for intravenous injection.

In an aspect, the injection formulation may be a solution in which a freeze-dried peptide was dissolved in saline.

In an aspect, the peptide concentration in the solution may be from 0.5 to 1.0 mg/mL.

In an aspect, the peptide may be administered in the dose of 0.5 to 5.0 mg/kg at 1 time.

In an aspect, the peptide may be administered in a single dose.

Advantageous Effects

In an aspect, the present invention can be lowered cytokine concentrations remarkably related to sepsis.

In an aspect, the present invention can effectively prevent or treat sepsis.

In an aspect, the present invention can improve the symptoms of sepsis effectively.

In an aspect, the present invention can prevent or cure septic shock in advance.

DETAILED DESCRIPTION OF THE INVENTION

Best Mode

Septic shock means a serious infection and a result of sepsis, which can cause various organ dysfunction syndrome (multiple organ dysfunction syndrome (MODS)) and can lead to death.

Severe sepsis occurs when sepsis imports pulmonary dysfunction, blood clots or other blood disorders, decreased urine production, or mental status changes and organ dysfunction.

Organ dysfunction of severe sepsis causing blood pressure (hypotension) or diseases such as lactic acidosis is related to one or more organs of the insufficient blood flow, this is septic shock.

Sepsis is resulting from an organ dysfunction, changes in local blood flow, sepsis-induced hypotension (<90 mmHg or decrease from baseline of >40 mmHg), the widespread intravascular coagulation.

One of the factors appeared to promote the development of MODS in patients with sepsis is cytokine-induced disorders observed as fine microcirculatory vascular thrombosis.

Produced from bacterial endotoxin and cytokines, in particular TNF, IL-1 and IL-6 cause damage to the endothelium by activating agglomeration(procoagulation) factors at endothelial.

The damaged endothelial surface may cause, as well as anti-fibrinolytic to inhibit the aggregation properties (anti-fibrinolysis) by increasing the blood coagulation, vascular thrombosis fine (thrombosis) and multiple organ failure.

Thus, TNF, IL-1 and IL-6 which are capable of inhibiting drug, such as a cytokine is effective to improving the symptoms of sepsis, or the treatment or prevention of sepsis.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells.

In an aspect, the present invention relates to a composition, the composition may comprise a peptide or fragment thereof of a peptide having a peptide comprising the amino acid sequence of SEQ ID NO: 1, at least 80% sequence homology with the peptide sequence.

In an aspect, the present invention relates to a method, the method comprising the peptide or fragment thereof in the prevention of sepsis peptide comprising a peptide having the amino acid sequence of SEQ ID NO: 1 in the amount effective, at least 80% sequence homology with the peptide sequence or a method of treatment or prevention of sepsis comprising administering to a subject in need of treatment.

In an aspect, the invention relates to a use, the invention is the use of the amino acid sequence comprising SEQ ID NO: 1 peptide, wherein the peptide sequence having at least 80% sequence homology to the peptide or peptide fragment thereof in the prevention or treatment of sepsis.

In an aspect, the present invention relates to a peptide, wherein the peptide is the peptide for the prevention or treatment of sepsis comprising the amino acid sequence of SEQ ID NO: 1 peptide, wherein the peptide sequence having at least 80% sequence homology to the peptide or peptide fragment thereof that.

In an aspect, the present invention relates to a kit, the kit may include the amino acid sequence comprising SEQ ID NO: 1 peptide, wherein the peptide sequence having at least 80% sequence homology to the peptide or peptide fragment thereof; dose of the peptide, the route of administration, dosage and the one or more of the indications.

In an aspect, the fragment can be a fragment composed of three or more amino acids.

In another aspect, the fragments may be composed of at least 4, 5 or more, 6 or more, 7 or more, 8 or more, 9 or more, 10 or more, 11 or more, 12 or more, 13 or more, 14 or more or 15 or more amino acids.

In an aspect, the peptides may be derived from the human telomerase.

Specifically, the peptide of SEQ ID NO: 1 refers to a peptide of position 611 to 626 of the entire human telomerase sequence (1132 amino acids, SEQ ID NO: 2).

In an aspect, prevention or treatment of the sepsis can be to prevent or 세 treat the septic shock.

In an aspect the peptide may be administered in the form of injection formulation but are not limited.

In an aspect the injection formulation may be an intravenous injection formulation.

In an aspect, the injection formulation may be a saline solution which a freeze-dried peptide was dissolved in In an aspect, the peptide concentration in the solution may be from 0.5 to 1.0 mg/mL.

In another aspect, the peptide concentration in the solution is 0.6 mg/mL or more, or may be more than 0.7 mg/mL.

In another aspect, the solution of 0.8 mg/mL of peptide concentrations may be less than or less than 0.9 mg/mL.

For example, 0.75 mg/mL can be.

In an aspect the peptide may be administered once at a dose of 0.5 to 5.0 mg/kg.

In an aspect, the single dose is 0.6 mg/kg or more, 0.7 mg/kg or more, 0.8 mg/kg or more, 0.9 mg/kg or more, 1.0 mg/kg or more, 1.1 mg/kg or more, 1.2 mg/kg or more, 1.3 mg/kg or more, can be 1.4 mg/kg or more.

The dosage may be 4.5 mg/kg or less, 4.0 mg/kg or less, 3.5 mg/kg or less, 3.0 mg/kg or less, 2.5 mg/kg or less, 2.0 mg/kg or less, 1.8 mg/kg or less.

In an aspect the peptide may be administered in a single dose.

Sepsis is necessary to administer relatively high doses at short intervals because of acute inflammation.

The effect of a peptide comprising the amino acid sequence of SEQ ID NO: 1, the peptide having at least 80% sequence homology with the peptide sequence or the fragment of the peptide is very excellent even when the administration frequency is once, when the dose is 0.5 to 5.0 mg/kg.

But it is not necessarily limited to a single dose.

If necessary, the dosages of 0.5 and 5.0 mg/kg may be administered two or more times.

Further, in some cases, it may also increase the number of lower doses administered.

For example, lowering the dose of from 0.1 to 1.0 mg/kg, administered two or more times instead of the number of times, three times or more or at least four times, the administration interval for more than 30 minutes, 1 hour or more, and less than 2 hours or 3 hours may also be administered.

In an aspect, the composition may be a pharmaceutical composition.

In another aspect, the composition may be a food composition.

Sepsis and related symptoms as used herein, "substantially removed" means that is for reducing the occurrence of the symptoms of at least 96%.

As used herein, "treating" include, for example, the suppression of disorder, degeneration, or causing the congestion, or to reduce the severity of disorder, suppressing, inhibiting, and reduce or remove the symptoms of the disorder or to improve the symptoms.

As used herein, "suppression" of the disease progression or disease complications in a subject means that the disease progression and/or to prevent or reduce disease in a subject complications.

As used herein, the "Symptoms" and related sepsis includes any clinical signs associated with arthritis, or test, not limited to subjects feel or observed.

Inflammation can be a symptom of sepsis.

One aspect of the invention provides a polynucleotide encoding the peptide or fragments thereof which are peptides having a peptide comprising the SEQ ID NO: 1, SEQ ID NO: 80% or more homology with the peptide sequence.

By using the polynucleotide, the peptide comprising the sequence SEQ ID NO: 1 or the fragment or a peptide having the peptide sequence with at least 80% homology can be mass-produced.

For example, a vector including a polynucleotide encoding a peptide may be inserted into a host cell and the host cell may be cultured to produce the peptide at a large scale The peptides disclosed herein can include a peptide comprising an amino acid sequence above 80%, above 85%, above 90%, above 95%, above 96%, above 97%, above 98%, or above 99% homology. Moreover, the peptides disclosed in the present invention can include a peptide comprising SEQ ID NO: 1 or its fragments, and a peptide with more than 1 transformed/substituted amino acid, more than 2 transformed/substituted amino acids, more than 3 transformed/substituted amino acids, more than 4 transformed/substituted amino acids, more than 5 transformed/substituted amino acids, more than 6 transformed/substituted amino acids, or more than 7 transformed/substituted amino acids.

According to an embodiment of the present invention, changes in amino acid sequence belong to the modification of peptide's physical and chemical characteristics. For example, amino acid transformation can be performed by improving thermal stability of the peptide, altering substrate specificity, and changing the optimal pH.

The term "amino acid" herein includes not only the 22 standard amino acids that are naturally integrated into peptide but also the D-isomers and transformed amino acids.

Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, palmitoylation), alkylation, carboxylation, hydroxylation, glycation, biotinylation, ubiquitinylation, transformation in chemical properties (e.g. β-removing deimidation, and deamidation), and structural transformation (e.g. formation of disulfide bridge). Also, changes of amino acids are included, such as changes of an amino group, a carboxyl group, or a side chain that occur due to chemical reactions during the combination process with crosslinkers for formation of a peptide conjugate.

A peptide disclosed herein may be a wild-type peptide that has been identified and isolated from natural sources. On the other hand, when compared to peptide fragments of SEQ ID NO: 1, the peptides disclosed herein may be artificial mutants that comprise one or more substituted, deleted, and/or inserted amino acids. Amino acid alteration in wild-type polypeptide—not only in artificial mutants—comprises conservative substitution of amino acids that do not significantly influence protein folding and or activation. Examples of conservative substitution belong to the group consisting of basic amino acids (arginine, lysine, and histidine), acidic amino acids (glutamic acid and aspartic acid), polar amino acids (glutamine and asparagines), hydrophobic amino acids (leucine, isoleucine, valine, and methionine), aromatic amino acids (phenylalanine, tryptophan, and tyrosine), and small amino acids (glycine, alanine, serine, and threonine). The amino acid substitutions that do not generally alter the specific activity are known in the art of the present invention. Most commonly occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations. Other examples of conservative substitutions are shown in the following table 1:

TABLE 1

| Original amino acid | Examples of residue substitution | Preferable residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial transformation of the biological properties of peptides are performed by selecting a significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:

(1) hydrophobicity: Norleucine, met, ala, val, leu, ile;
(2) neutral hydrophilicity: cys, ser, thr;
(3) acidity: asp, glu;
(4) basicity: asn, gin, his, lys, arg;
(5) residue that affects chain orientation: gly, pro; and
(6) aromaticity: trp, tyr, phe.

Non-conservative substitutions may be performed by exchanging a member of the above classes to that of a different class. Any cysteine residues that are not related in maintaining the proper three-dimensional structure of the peptide can typically be substituted into serine, thus increasing the oxidative stability of the molecule and preventing improper cross-linkage. Conversely, improvement of stability can be achieved by adding cysteine bond(s) to the peptide.

Altered types of amino acids variants of peptides are those that an antibody glycosylation pattern changed. The term "change" herein relates to deletion of carbohydrate residues and/or addition of at least one glycosylated residue that does not exist within a peptide.

Glycosylation in peptides are typically N-connected or O-connected. The term "N-connected" herein relates to that carbohydrate residues are attached to the side chain of asparagine residues. As tripeptide sequences, asparagine-X-serine and asparagine-X-threonine (where the X is any amino acid except proline) are the recognition sequences for attaching carbohydrate residue enzymatically to the side chain of asparagine. Therefore, with the presence of one of these tripeptide sequences in a polypeptide, the potential glycosylation sites are created. "O-connected glycosylation" means attaching one sugar selected from N-acetylgalactosamine, galactose, or xylose to hydroxyl amino acids. The hydroxyl amino acids are most typically serine or threonine, but 5-hydroxyproline or 5-hydroxylysine can be used.

Addition of a glycosylation site to a peptide is conveniently performed by changing an amino acid sequence to contain a tripeptide sequence mentioned above (for N-linked glycosylation sites). These changes may be made by addition of at least one from serine or threonine residues to the first antibody sequence, or by substitution with these residues (for O-linked glycosylation sites).

In another aspect herein embodiment provides, nucleic acid molecule encoding the above polypeptide, the nucleotide sequence thereof has, for example GAA GCG CGC CCG GCG CTG CTG ACC AGC CGC CTG CGC TTT ATT CCG AAA SEQ ID NO: (SEQ ID NO: 3).

The nucleic acid molecule can be introduced in the host cell according to known techniques.

For example, calcium phosphate method, a liposome, electroporation, viruses, and cells transformed by being brought into contact with, or directly into cells by micro-injection method, and the like.

Host cell is a higher eukaryotic cell, such as mammalian cell, or a lower eukaryotic cell, for example, yeast cells, or prokaryotic cells or, for example, may be a bacterial cell.

Suitable prokaryotic hosts for transformation can be exemplified as *E. coli, Bacillus subtilis, Salmonella typhimurium, Pseudomonas, Streptomyces*, microbacterial species belonging to the genus.

A vector comprising nucleic acid molecules typically may include origin of replication that allows the transformation of a host cell with a recombinant expression vector and a selectable marker (e.g., Dihydro folate reductase or neomycin resistance for eukaryotic cell culture, or Tetracycline or ampicillin resistance in *E. coli*, or the *S. cerevisiae* TRP1 gene), and promoter to control transcription of protein coating sequence.

Useful expression vectors are, for example, derivatives of SV40 and pcDNA and col E1, pCR1, pBR322, pMal-C2, pET, pGEX (Smith, et al., Gene 67:31-40 (1988)) such as known bacterial plasmid, pMB9 and plasmids such as RP4 and its derivative, phage DNA, such as the numerous derivatives of phage NM989 I like, and M13 and filamentous phage such as phage DNA, single-stranded DNA; yeast plasmid, for example, phage DNA or vectors derived from combinations of plasmids and phage DNA modified in order to use the expression control sequence.

Mammalian expression vector includes replication origin, a suitable promoter and enhancer.

Also it can includes essential ribosome binding site, a polyadenylation site, splice donor and acceptor sites, transcriptional termination sequences, and 5' flanking sequences.

Mammalian expression vectors include an inducible promoter, such as dihydro folate reductase vector comprising a promoter, any expression vector comprising DHFR cassette or pED such as DHFR/methotrexate co-amplification vector (Randal J, Kaufman, 1991, Randal J. Kaufman, Current Protocols in Molycular Biology, 16, 12 (1991)).

Or glutamine synthetase/methionine sulfoxide thymine co-amplification vector, such pEE14 (Celltech).

Indicating an expression vectors under the control of the episomal Epstein-Barr virus (EBV) or nuclear antigen (EBNA), for example, pREP4 (Invitrogen), pCEP4 (Invitrogen), pMEP4 (Invitrogen), pREP8 (Invitrogen), pREP9 (Invitrogen), and pEBVHis (Invitrogen) can be used.

Selective mammalian expression vectors are Rc/CMV (Invitrogen), pRc/RSV (Invitrogen) and the like.

The vaccinia virus mammalian expression vectors which can be used in this invention are pSC11, pMJ601, pTKgptF1S and the like.

The yeast expression systems which can be used in this invention include the non-fusion pYES2 vector (Invitrogen), the fusion pYESHisA, B, C (Invitrogen), pRS vectors and the like.

The vector may be introduced into a mammalian cells particularly derived from human cell, or bacteria, yeast, fungi, insects, nematode and plant cells.

Examples of suitable cells are, VERO cells, HELA cells such as ATCC No. ATCC No. CCL2, CHO cell lines, such as CCL61, COS cells such as COS-7 cells and ATCC No. CRL 1650 cells, W138, BHK, HepG2, 3T3, for example ATCC No. CRL6361, A549, PC12, K562 cells, 293 cells, Sf9 cells such as ATCC No. CRL1711 and Cv1 cells such as ATCC No. CCL70, and so on.

Any other suitable cells used in this invention are prokaryotic host cells strains such as *Escherichia coli* (e.g., strain DH5-α), *Bacillus subtilis, Salmonella typhimurium*, or *Pseudomonas*, Strains belonging to the genus *Streptomyces* and *Staphylococcus*.

According to an embodiment of the present invention, provided is a pharmaceutical composition or a food composition, which effectively delivers active components into cells, the pharmaceutical composition or the food composition including a peptide comprising an amino acid sequence of SEQ ID No.: 1 or a fragment peptide thereof, an HSP binding peptide comprising an amino acid sequence having a sequence identity of 80% or greater to the amino acid sequence, and a conjugate of an active component.

According to an embodiment of the present invention, the composition may contain 0.1 μg/mg to 1 mg/mg, specifically 1 μg/mg to 0.5 mg/mg, more specifically 10 μg/mg to 0.1 mg/mg of a peptide comprising an amino acid sequence of SEQ ID NO: 1, a peptide comprising an amino acid sequence having a sequence identity of 80% or greater to the amino acid sequence, or a peptide fragment thereof. When the peptide is contained in the above-mentioned range, all the safety and stability of the composition may be satisfied and cost-effectiveness may be achieved.

According to an embodiment of the present invention, the composition may have applications to all animals including humans, dogs, chickens, pigs, cows, sheep, guinea pigs, and monkeys.

According to an embodiment of the present invention, a pharmaceutical composition may be administered through oral, rectal, transdermal, intravenous, intramuscular, intraperitoneal, intramedullary, epidural, or subcutaneous means.

Forms of oral administration may be, but not limited to, tablets, pills, soft or hard capsules, granules, powders, solutions, or emulsions. Forms of non-oral administration may be, but not limited to, injections, drips, lotions, ointments, gels, creams, suspensions, emulsions, suppositories, patches, or sprays.

According to an embodiment of the present invention, the pharmaceutical composition, if necessary, may contain additives, such as diluents, excipients, lubricants, binders, disintegrants, buffers, dispersants, surfactants, coloring agents, aromatics, or sweeteners. According to an embodiment of the present invention, the pharmaceutical composition may be manufactured by conventional methods of the industry in the art.

According to an embodiment of the present invention, the active ingredient of the pharmaceutical composition may vary according to the patient's age, sex, weight, pathology state and severity, administration route, or prescriber's judgment. Dosage may be determined by one of ordinary skill in the art based on the above-mentioned factors, and the daily dose may be, but is not limited to, about 0.1 μg/kg/day to about 1 g/kg/day, specifically about 1 μg/kg/day to about 10 mg/kg/day, more specifically about 10 μg/kg/day to about 1 mg/kg/day, and more specifically about 50 μg/kg/day to about 100 μg/kg/day. According to an embodiment of the present invention, the pharmaceutical composition may be administered, but is not limited to, 1 to 3 times a day.

According to an embodiment of the present invention, a cosmetic composition suitable for topical application can be provided with all formulation.

For example, it can be provided with a solution, emulsion obtained by dispersing the oil phase in the aqueous phase, emulsion obtained by dispersing the aqueous phase in the oil phase, a suspension, a solid, a gel, a powder, a paste, a foam(foam), or the aerosol formulation.

Such formulations can be produced according to a conventional method.

According to an embodiment of the present invention, the cosmetic composition within a range not impairing the effect, preferably the composition can include other ingredients which can synergistic effects on the main effect.

In addition, according to an embodiment of the present invention, the cosmetic composition may include a moisturizing agent, emollient agent, surfactant, ultraviolet absorbent, antiseptic, fungicide, antioxidant, pH regulator, an organic or inorganic pigment, fragrance, feeling of cold, or restriction.

The amount of the above components of the invention can be selected in the range of not damaging the objects and effects, and the amount of the above components can be the 0.01 to 5% by weight, in particular 0.01 to 3% by weight.

According to an embodiment of the present invention, food composition is not limited in its formulations, but the food composition may be tablets, granules, powder, liquid formulations, or solid preparations. In addition to the active ingredients, each formulation may be prepared with ingredients commonly used in the industry and appropriately chosen by those skilled in the art, and effects of the formulation may increase when the formulation is applied simultaneously with other ingredients.

Determination of a dosage of the above-mentioned active ingredient may be known by one of ordinary skill in the art, and a daily dosage may be about 1 μg/kg/day to about 10 mg/kg/day, more specifically about 10 μg/kg/day to about 1 mg/kg/day, and more specifically about 50 μg/kg/day to about 100 μg/kg/day. However, the daily dosage is not limited to these numbers and may vary according to other various factors such as age, health status, and complications of the subject of administration.

Forms of oral administration may be, but not limited to, solid or liquid dosage unit, for example powders, discutients, tablets, sugarcoated pills, capsules, granules, suspensions, solutions, syrups, drop agents, sublingual tablet other formulations.

Forms of powders are produced by pulverizing the compound of the present invention to an appropriate particle size. Forms of discutients are also produced by pulverizing the compound of the present invention and mixing with pharmaceutical carriers, for instance carbohydrates such as starch and mannitol pulverized to an appropriate particle size. If necessary, forms of powders may contain additives, such as excipients, preservatives, dispersants, coloring agents, aromatics or others.

Forms of granules as described above are produced by filling in a capsule shall such as gelatin capsule with forms of powders, discutients or tablets. After forms of lubricants or fluidizing agents such as colloidal silica, talk, magnesium stearate, calcium stearate, and solid polyethylene glycol are mixed to forms of powders, the operation of filling may make progress. Adding the forms of disintegrants or solubilizer such as carboxymethyl cellulose, carboxymethyl cellulose calcium, low level substituted hydroxypropyl cellulose, crosscarmellose sodium, carboxymethyl starch sodium, calcium carbonate, sodium carbonate may increase an effectiveness of a drug when the forms of capsules are taken.

Also, forms of micro powder of the present invention may be soft capsules made by dispersing in plant oil, polyethylene glycol, glycerin, and surfactant and covering with gelatin sheets.

Forms of tablet are made by adding excipients to create powder mixture, being granulation or slug, and tableting after adding lubricant.

If necessary, the dose prescription for oral administration may be a microcapsule. The prescription may also arouse time delay or sustain release by covering with sheath or dipping in polymer or wax.

Forms of non-oral administration may use injection, suppository and etc. For subcutaneous, muscle, or vein injection, a single dose unit such as forms of solution or suspension may be used. They are made by dissolving part of compound in non-toxic liquid carrier that is suitable for injection, and sterilizing the solution or suspension. In order to make the solution of injection isotonic solution, non-toxic salt or salt-solution may be added. Also, stabilizers, preservatives, emulsifiers may be used in combination.

Rectal administration may use a suppository made by dissolving the compound of the present invention in the mixture comprising solid having low melting point and being soluble or insoluble in water such as polyethylene glycol, cacao butter, semi synthetic lipid, poly ester (e.g. palmitic myristyl ester).

The composition for preventing and treating rheumatoid arthritis according to the present invention may be used in mixture or combination with other drugs such as anti-inflammatory steroid, non-steroidal anti-inflammatory drug, immunosuppressant, disease modification anti-rheumatism drug.

The terms used herein is intended to be used to describe the embodiments, not to limit the present invention. Terms without numbers in front are not to limit the quantity, but to show that there may be more than one thing about the term used. The terms "comprising", "having", "including" and "containing" shall be interpreted openly (i.e. "including but not limited to").

Mention of a numerical range is used instead of stating separate numbers within the range, so unless it is explicitly stated, the range should be construed as if all the numbers within the range are separately described herein. The end values of all the ranges are included in the range and can be combined independently.

Unless otherwise noted or clearly contradicting in context, all methods mentioned herein can be performed in a proper order. The use of any one embodiment and all embodiments, or exemplary language (e.g., "such as", "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have the meanings ordinarily understood by a person skilled in the art that the present invention belongs to.

The preferred embodiments of the present invention include the best mode known to the inventors to perform the present invention. Variations in the preferred embodiments can become clear to those skilled in the art after reading the statements above. The present inventors hope that those skilled in the art can use the variations adequately and present invention be conducted in other ways than listed herein. Thus, the present invention, as allowed by the patent law, includes equivalents, modifications and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

EXAMPLES

Example 1

Synthesis of Peptide

The peptide of SEQ ID NO: 1 was synthesized according to the conventionally known method of solid phase peptide synthesis. More specifically, the peptide was synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to a resin were used as follows:
NH2-Lys(Boc)-2-chloro-Trityl Resin
NH2-Ala-2-chloro-Trityl Resin
NH2-Arg(Pbf)-2-chloro-Trityl Resin All the amino acids to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in an acid. Examples include the followings:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. Piperidine in 20% DMF was used to remove Fmoc. In order to remove the protection from residues or to separate the synthesized peptides from Resin, cleavage cocktail [TFA (trifluoroacetic acid)/TIS (triisopropylsilane)/EDT (ethanedithiol)/H2O=92.5/2.5/2.5/2.5] was used.

The peptide synthesis was performed by using solid phase scaffold with the repetition of the following processes: starting with the amino acid protection, separate reaction of each amino acid, washing with solvents, and deprotection. Each peptide was synthesized by using the solid phase scaffold combined to starting amino acid with the amino acid protection, reacting the corresponding amino acids separately, washing with a solvent and deprotected, and repeating the processes. Upon the release from the resin, the synthesized peptides were purified by HPLC, validated by Mass Spectrometry, and freeze-dried, and verify for synthesis by MS, and then freeze-dried.

The purity of the prepared peptide was found to be 95% or higher by high-performance liquid chromatography.

Specific peptide synthesis process is described as the following based on the synthesis process of PEP 1 which has SEQ ID: NO. 1.

1) Coupling

The amino acid (8 equivalent) protected with NH2-Lys(Boc)-2-chloro-Trityl Resin, and coupling agent HBTU(8 equivalent)/HOBt(8 equivalent.)/NMM(16 equivalent) melted in DMF were mixed together, and incubated at room temperature (RT) for 2 hr. Following the incubation, the reaction mixture was subjected to the sequential washes of DMF, MeOH, and DMF.

2) Fmoc Deprotection

Piperidine in 20% DMF was added and incubated at RT for 5 minutes 2 times, then sequentially washed with DMF, MeOH, and DMF.

3) Making the basic framework of peptide, NH2-E (OtBu)-A-R(Pbf)-P-A-L-L-T(tBu)-S(tBu)-R(Pbf)L-R(Pbf)-F-I-P-K(Boc)-2-chloro-Trityl Resin) by repeating the above mentioned-reactions 1) and 2).

4) Cleavage: Cleavage Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

Example 2

Preparation of Formulation

1. PEP 1 Preparation of the Intravenous Formulation

The PEP 1 of the freeze-dried powder form obtained according to Example 1 was used and dissolved in 0.9% saline.

PEP 1 of correction for purity (purity: 97.3%, content: 85.3%) was prepared by conducting the injectable solutions in a concentration of 0.75 mg/mL with 0.9% sodium chloride solution as an excipient just before administration.

2. LPS Intravenous Preparations of Formulation

As Lipopolysaccharide (lipopolysaccharide, LPS), *Escherichia coli* (*E. coli*) O127: B8 (ATCC 12740) (Sigma-Aldrich Co., St. Louis, Mo., USA, L3129) of LPS were used.

LPS also using a 0.9% saline immediately before the administration was prepared by dissolving a 0.25 mg/mL capacity.

Example 3

Animal Experiments

In this experiment, the Corporation Korea Institute of Animal Science and Animal experiments were conducted in compliance with the Code of Ethics.

In addition, this experiment as the Non GLP test was carried out with the Food and Drug Administration Announcement No. 2009-183 (Dec. 22, 2009) "Non-standard clinical trial management, and OECD Principles of Good Laboratory Practice (1997).

In this experiment, after causing the inflammation associated with sepsis in Sprague-Dawley rat administered with the test substance, and then the PEP 1 blood nitric oxide (NO), and cytokines were measured.

Used Sprague-Dawley rat was a specific pathogen-free SPF rats which was obtained from Orient Bio (Gyeonggi-do, Republic of Korea Gapyeong mokdongri Buk-myeon).

8.5 weeks old, among 100 male rats with a body weight less than 250 g±20%, observations of seven days, 96 healthy males (mean 9.5 weeks, mean body weight (g) of ±20% or less) became targets of experiment which was carried out.

Breeding conditions were temperature 23±3° C., relative humidity 55±15%, the number of ventilation 10-20 times/hr, lighting time 12 hours (8:00 am to 8:00 pm lights off) and 150~300 Lux Illumination.

Divide the 48 rats in all four groups were administered the PEP 1 and/or LPS for each group.

All routes of administration were intravenous administration.

Specifically, the exemplary formulations and PEP 1 prepared in Example 2/or the LPS was administered by intravenous injection formulation.

Both times were administered once.

The dose was administered by calculating 2 mL/kg on the basis of the measured weight before administration to the last Dosage of each group was carried out as in the following Table.

TABLE 2

| No | Dose (mg/kg) PEP 1 | LPS | Injection formulation dosage (mL/kg) | Number of animals |
|---|---|---|---|---|
| G1 | — | — | 2 | 12 |
| G2 | 1.5 | — | 2 | 12 |
| G3 | — | 0.5 | 2 | 12 |
| G4 | 1.5 | 0.5 | 2 | 12 |

First, PEP 1 for all animal and/or blood sample was collected before administration of LPS on the day before by 0.8 mL.

All subjects were bled on the following day for the first administration of LPS administered according to the above table, LPS after 30 minutes from the time of administration, PEP 1 dose administration was performed for the subject group.

Dosages were as indicated in the table.

After completion of the administration of LPS administered every 75 minutes and 255 minutes from the time (i.e., PEP 1 from the time of administration of each 45 minutes and 195 minutes) at each blood sample was 0.8 mL.

With respect to the sampling of blood was used for analyzing cytokines.

TNF-α, IL-1b and IL-6 concentrations were measured which were the main indicator of cytokines in sepsis.

For G1~G4 in Table 1, TNF-α, IL-1, IL-6 concentration was measured.

Figure 1:
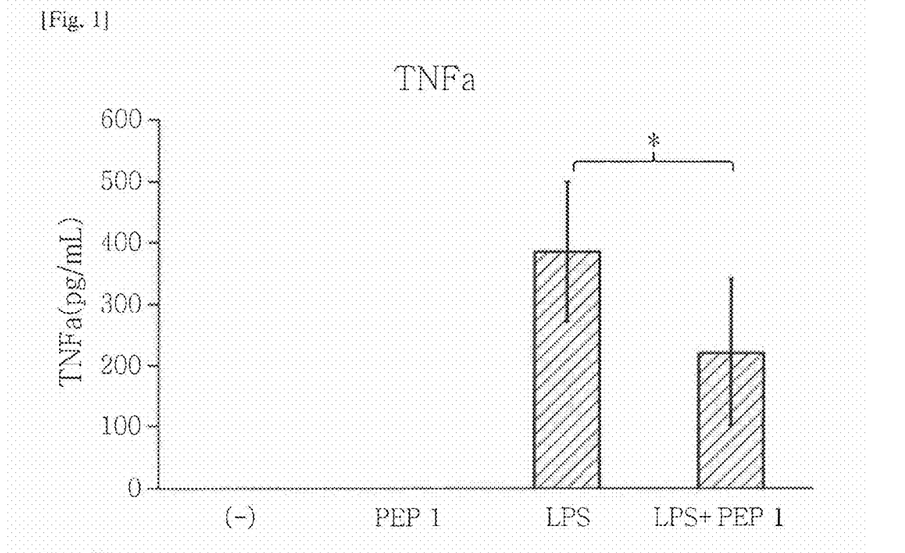
FIG. 1 shows a result of measuring the concentration of the TNF-α by measuring the concentration in blood sample after each PEP 1, LPS, and LPS+PEP 1 was administered to the rat in accordance with Table 1.
Figure 2:
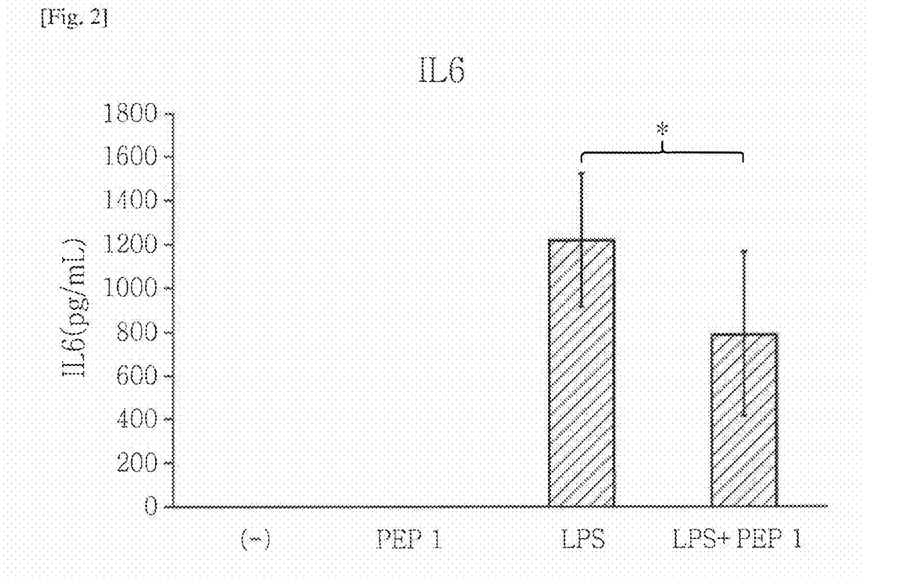
FIG. 2 shows a result of the concentration of IL6 by measuring the concentration in blood after each PEP 1, LPS, and LPS+PEP 1 was administered to rats in accordance with Table 2.
Figure 3:
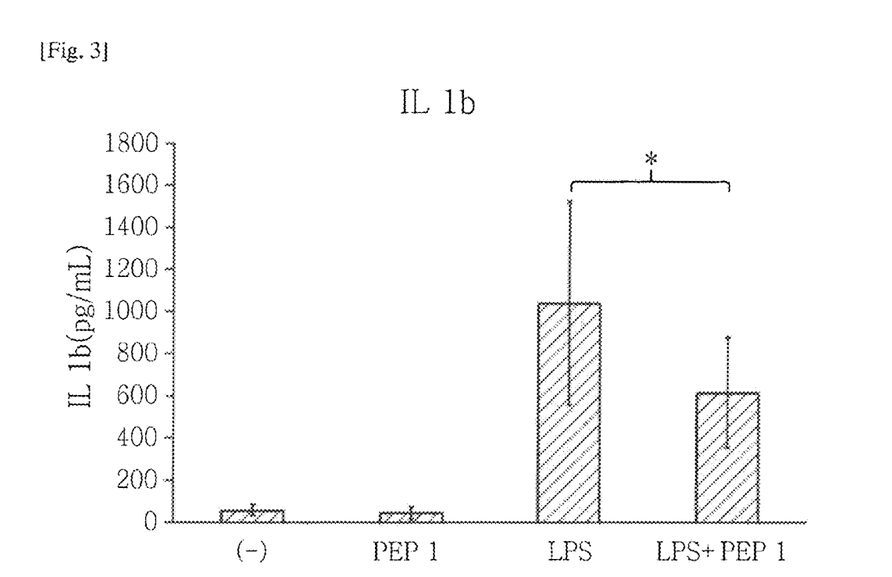
FIG. 3 shows a result of the concentration of IL1b by measuring the concentration in blood after each PEP 1, LPS, and LPS+PEP 1 was administered to rats in accordance with Table 2.

The results are shown in FIGS. 1 to 3.

"*" Means $p<0.05$ shown in Fig.

FIG. 1 is a result of blood after the administration of each PEP 1, LPS, and LPS+PEP 1 in accordance with Table 1, and measuring the concentration of TNF-α blood.

As shown in FIG. 1, blood of rats with LPS induced sepsis has TNF-α present in a high concentration, but after the LPS administration, the concentration of TNF-α in the blood of rats as a result only 195 minutes handle PEP 1 can be seen significantly reduced FIG. 2 is a result of blood after the administration of each PEP 1, LPS, and LPS+PEP 1 in accordance with Table 2 shows the results of measuring the concentration of blood IL6.

As shown in FIG. 2, blood of rats with LPS induced sepsis is present in a high concentration of the IL6, but the IL6 after LPS administration, the concentration of the blood of the rats in the results of IL6 only 195 minutes treated with PEP 1 can be seen significantly reduced.

FIG. 3 is a result of the concentration in the blood after the administration of LPS+PEP 1 to draw blood by measuring the concentration of blood IL1b in accordance with Table 2.

As shown in FIG. 3, the concentration of IL1b is high in the blood of rats induced sepsis, but after administration of LPS and PEP1, the concentration of IL1b in the blood of rats is significantly reduced only after 195 minutes.

On the other hand, a single dose of 1.5 mg/kg, all rats were found to be alive.

Example 4

Toxicity (1) Cell Culture

HeLa cell line was purchased from ATCC. The HeLa cell line was maintained in MEM supplemented with 10% fetal bovine serum (Invitrogen, USA), Earle's salts, non-essential amino acids, sodium pyruvate, 100 μg/ml penicillin and 100 units/ml streptomycin, and then incubated at 37° C., 5% CO2.

(2) Cell Viability and Toxicity Analysis

Figure 4:
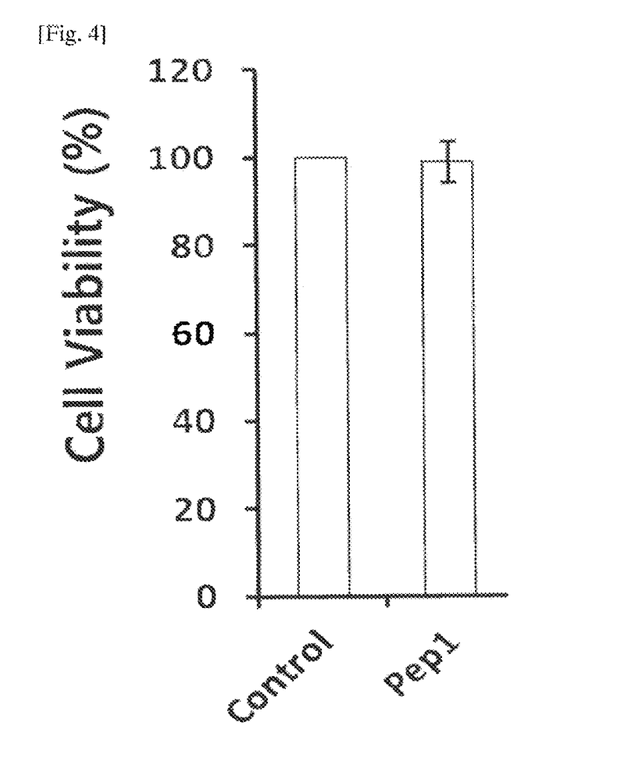
FIG. 4 shows a result of a toxicity test within HeLa cells.

The cells were seeded into 96-well plates and added to each well for medium supplemented with 10% fetal bovine serum (Invitrogen, USA), 100 ug/ml penicillin and 100 units/ml streptomycin. The cells were cultured in 37° C., 5% CO2 for 12 h incubator. After incubated, plates washed by PBS, and added MEM(Minimum essential medium) for starvation during 1 h. The 20 uM of PEP 1 with 100 uL of the aqueous solution were added to each well, and then the cells were incubated at 37° C. for 24. After incubated, the cell viability and toxicity were evaluated using an MTT assay. The result is shown in FIG. 4.

What is claimed is:

1. A method for preventing or treating sepsis comprising administering to a subject in need thereof the isolated peptide of SEQ ID NO: 1.

2. The method according to claim 1, wherein the peptide is administered in a single dose at a concentration of 0.1 μg/kg to 1.0 g/kg.

3. The method according to claim 1, wherein the peptide is administered in a single dose at a concentration of 1 μg/kg to 10 mg/kg.

4. The method according to claim 1, wherein the peptide is administered 1 to 3 times a day.

5. The method according to claim 4, wherein the peptide is administered at a daily dose of 0.1 μm/kg to 1.0 g/kg.

6. A method for preventing or treating sepsis comprising administering to a subject in need thereof a composition comprising the isolated peptide of SEQ ID NO: 1.

7. The method of claim 6, wherein the composition is administered through oral, rectal, transdermal, intravenous, intramuscular, intraperitoneal, intramedullary, epidural, or subcutaneous routes.

8. The method of claim 6, wherein the composition comprises 0,1 μg/ing to 1 mg/mg of isolated peptide.

9. The method of claim 6, wherein the peptide is administered in a single dose at a concentration of 0.1 μg/kg to 1.0 g/kg.

10. The method of claim 6, wherein the peptide is administered in a single dose at a concentration of 1 μg/kg to 10 mg/kg.

11. The method of claim 6, wherein the peptide is administered 1 to 3 times a day.

12. The method of claim 11, wherein the peptide is administered at a daily dose of 0.1 μg/kg to 1.0 g/kg.

* * * * *